(12) United States Patent
Wolinsky et al.

(10) Patent No.: US 6,730,116 B1
(45) Date of Patent: May 4, 2004

(54) MEDICAL DEVICE FOR INTRALUMINAL ENDOVASCULAR STENTING

(75) Inventors: Lone Wolinsky, Ramat Gan (IL); Amir David Loshakove, Moshav Burgata (IL); Arvi Penner, Tel Aviv (IL); Offer Nativ, Rishon LeZion (IL); Gil Naor, Ramat-Hasharon (IL); Niall Duffy, Co. Galway (IE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/292,991

(22) Filed: Apr. 16, 1999

(51) Int. Cl.$^7$ .................................................. A61F 2/06
(52) U.S. Cl. ..................... 623/1.16; 623/1.15; 623/1.11
(58) Field of Search ............................. 623/1.11, 1.15, 623/1.16, 1.1, 1.17, 1.34, 1.49

(56) References Cited

U.S. PATENT DOCUMENTS

| | | |
|---|---|---|
| 3,902,501 A | 9/1975 | Citron et al. |
| 4,531,243 A | 7/1985 | Weber et al. |
| 4,776,337 A | 10/1988 | Palmaz |
| 4,816,028 A | 3/1989 | Kapadia et al. |
| 4,856,516 A | 8/1989 | Hillstead |
| 4,893,623 A | 1/1990 | Rosenbluth |
| 4,969,458 A | 11/1990 | Wiktor |
| 4,994,071 A | 2/1991 | MacGregor |
| 5,019,085 A | 5/1991 | Hillstead |
| 5,080,674 A | 1/1992 | Jacobs et al. |
| 5,104,404 A | 4/1992 | Wolff |
| 5,116,365 A | 5/1992 | Hillstead |
| 5,135,536 A | 8/1992 | Hillstead |
| 5,178,618 A | 1/1993 | Kandarpa |
| 5,234,457 A | 8/1993 | Andersen |
| 5,282,824 A | 2/1994 | Gianturco |
| 5,293,879 A | 3/1994 | Vonk et al. |
| 5,306,250 A | 4/1994 | March et al. |
| 5,314,472 A | 5/1994 | Fontaine |
| 5,366,473 A | 11/1994 | Winston et al. |
| 5,383,892 A | 1/1995 | Cardon et al. |

(List continued on next page.)

FOREIGN PATENT DOCUMENTS

| | | |
|---|---|---|
| EP | 0679372 | 11/1995 |
| GB | 1205743 | 9/1970 |
| WO | 9503010 | 2/1995 |

OTHER PUBLICATIONS

"Inflection" The American Heritage Dictionary of the English Language, Third Edition, 1992 Houghton Mifflin Company, electronic version.*

*Primary Examiner*—Corrine McDermott
*Assistant Examiner*—Thomas Barrett
(74) *Attorney, Agent, or Firm*—Sterne, Kessler, Goldstein & Fox P.L.L.C.

(57) ABSTRACT

A medical device includes a catheter and a stent mounted on the catheter, the stent having a hollow, cylindrical body made with a plurality of rings. The rings each extend circumferentially around the cylindrical body and include an undulating series of peaks and valleys. The rings are joined together by a series of links which are shaped and arranged to promote longitudinal flexibility as the stent is delivered on the catheter and effective scaffolding after deployment. In one aspect of the invention, the rings are provided with inflection points on some portions of the rings which extend in a generally circumferential direction for a short distance. A link is joined at one end at the inflection point on one ring and also joined at a second end at a second inflection point on an adjacent ring. This construction allows the crimped stent to flex longitudinally when it is subjected to bending forces such as those encountered during delivery of the stent and catheter through a tortuous coronary artery.

56 Claims, 11 Drawing Sheets

U.S. PATENT DOCUMENTS

| | | |
|---|---|---|
| 5,389,106 A | 2/1995 | Tower |
| 5,421,955 A | 6/1995 | Lau et al. |
| 5,443,520 A | 8/1995 | Zweymuller et al. |
| 5,449,373 A | 9/1995 | Pinchasik et al. |
| 5,507,767 A | 4/1996 | Maeda et al. |
| 5,514,154 A | 5/1996 | Lau et al. |
| 5,527,354 A | 6/1996 | Fontaine et al. |
| 5,540,712 A | 7/1996 | Kieshinski et al. |
| 5,540,713 A | 7/1996 | Schnepp-Pesch et al. |
| 5,549,662 A | 8/1996 | Fordenbacher |
| 5,549,663 A | 8/1996 | Cottone, Jr. |
| 5,554,181 A | 9/1996 | Das |
| 5,556,413 A | 9/1996 | Lam |
| 5,591,197 A | 1/1997 | Orth et al. |
| 5,607,442 A | 3/1997 | Fischell et al. |
| 5,607,445 A | 3/1997 | Summers |
| 5,613,981 A | 3/1997 | Boyle et al. |
| 5,630,829 A | 5/1997 | Lauterjung |
| 5,632,771 A | 5/1997 | Boatman et al. |
| 5,636,641 A | 6/1997 | Fariabi |
| 5,643,312 A | 7/1997 | Fischell et al. |
| 5,653,727 A | 8/1997 | Wiktor |
| 5,681,346 A | 10/1997 | Orth |
| 5,697,971 A | 12/1997 | Fischell et al. |
| 5,725,570 A | 3/1998 | Heath |
| 5,725,572 A | 3/1998 | Lam et al. |
| 5,728,158 A | 3/1998 | Lau et al. |
| 5,733,303 A | 3/1998 | Israel et al. |
| 5,735,893 A | 4/1998 | Lau et al. |
| 5,741,327 A | 4/1998 | Frantzen |
| 5,755,776 A | 5/1998 | Al-Saadon |
| 5,759,192 A | 6/1998 | Saunders |
| 5,766,238 A | 6/1998 | Lau et al. |
| 5,776,161 A | 7/1998 | Globerman |
| 5,800,508 A | 9/1998 | Goicoechea et al. |
| 5,824,042 A | 10/1998 | Lombardi et al. |
| 6,042,605 A * | 3/2000 | Martin et al. .................. 623/1 |
| 6,066,169 A * | 5/2000 | McGuinness .............. 623/1.16 |
| 6,113,627 A * | 9/2000 | Jang .............................. 623/1 |

* cited by examiner

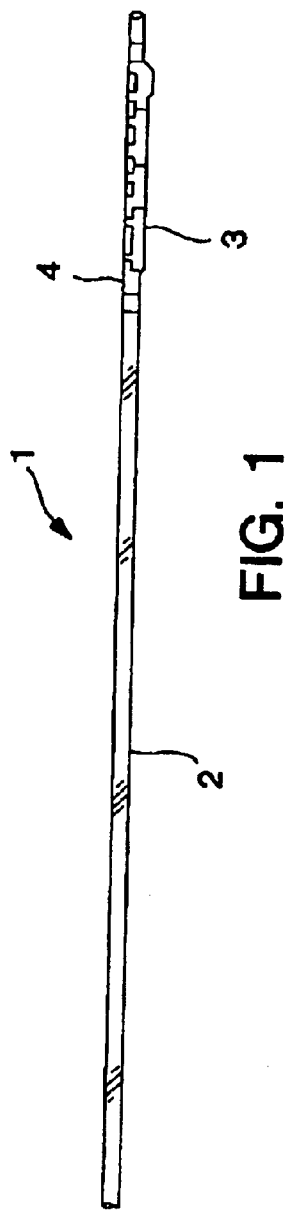
FIG. 1
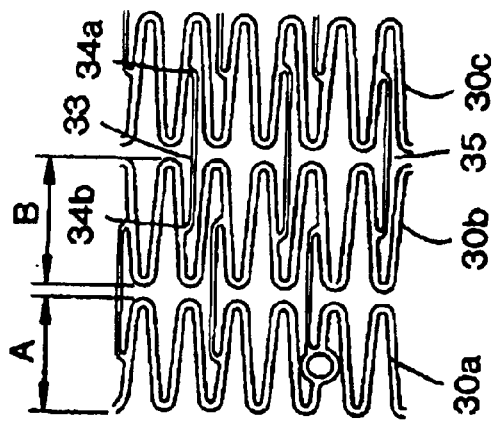
FIG. 4
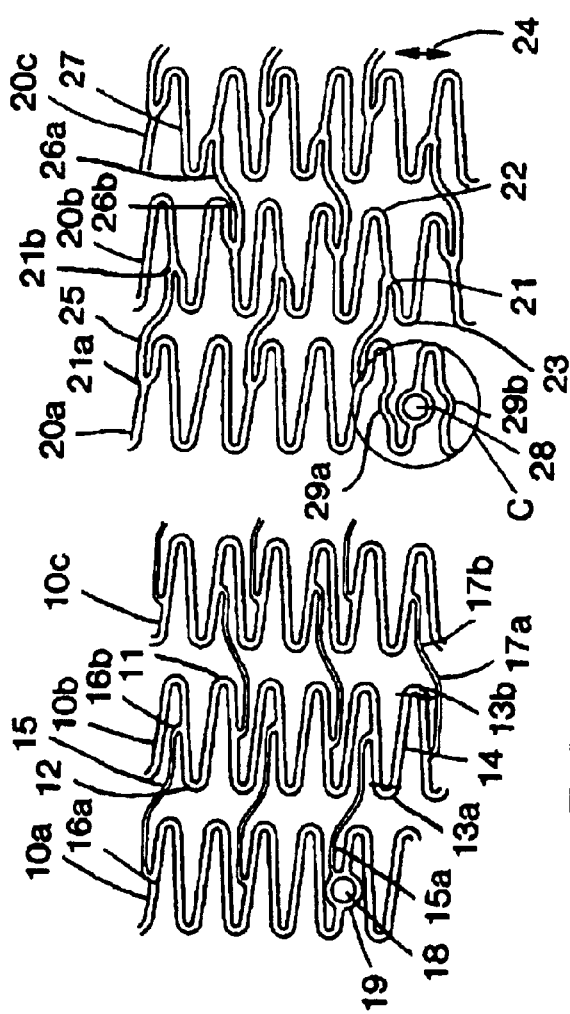
FIG. 3
FIG. 2

MEDICAL DEVICE FOR INTRALUMINAL ENDOVASCULAR STENTING

BACKGROUND OF THE INVENTION

This invention relates to intraluminal endovascular stenting, a method by which a prosthesis is inserted into a body tube and expanded so as to reopen a collapsed vessel wall and prevent the wall from recollapsing into the lumen. Endovascular stenting is particularly useful for arteries which are blocked or narrowed and is an alternative to surgical procedures that intend to bypass the occlusion.

Percutaneous transluminal coronary angioplasty (PTCA) is used to open coronary arteries which have been occluded by a build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from 1.5 mm in the coronary vessels to 30 mm in the aortic vessel.

A stent typically is a cylindrically shaped device formed from wire(s)or a tube and intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during an angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

A balloon of appropriate size and pressure is first used to open the lesion. The process is repeated with a stent crimped on a balloon. The stent is deployed when the balloon is inflated. The stent remains as a permanent scaffold after the balloon is withdrawn. A balloon capable of withstanding relatively high inflation pressures may be preferable for stent deployment because the stent must be forced against the artery's interior wall so that it will fully expand thereby precluding the ends of the stent from hanging down into the channel encouraging the formation of thrombus.

Previous structures used as stents or intraluminal vascular grafts have included coiled stainless steel springs; helical wound spring coil made from shape memory alloy; expanding metal stents formed in a zig-zag pattern; diamond shaped, rectangular shaped, and other mesh and non-mesh designs. Exemplary stent devices are disclosed in U.S. Pat. No. 5,776,161 issued to Globerman, U.S. Pat. No. 5,449,373 issued to Pinchasik et al, U.S. Pat. No. 5,643,312 issued to Fischell et al and U.S. Pat. No. 5,421,955 issued to Lau et al.

Problems to be overcome in stent design include inadequate radial force to maintain expansion; inadequate scaffolding of tissue to the wall; pre-dilated longitudinal rigidity which negatively impacts on stent delivery; and shortening of the stent as a consequence of radial expansion. Predilation stent longitudinal rigidity is a significant shortcoming, and prevents the threading of the stent through long tortuous vessels and lesions. Shortening of the stent is also a problem, as it is important that the stent cover the entire lesion to minimize the risk of post-operative complications. Many of these problems are the result of difficult design problems resulting from the often conflicting goals of stent design. For example, it is desirable to have a high degree of scaffolding in the stent when the stent is expanded to its rated radial size so that the vessel wall will have uniform support. However, it is also desirable to have a small, relatively smooth delivered profile when the stent is mounted on the catheter to permit the stent and catheter to traverse small diameter lesions. The person skilled in the art will appreciate that as a stent with a very small delivered profile expands radially its structural elements become farther apart and create openings which reduce the amount of scaffolding available to support the vessel. A similar situation exists with respect to the conflicting goals of improved scaffolding and flexibility during catheter delivery since proper scaffolding will not be accomplished if there are few supporting structural elements and yet a stent with too many structural elements may be difficult to crimp onto the balloon catheter such that the structural elements will not abut or interfere with each other during delivery through tortuous vessels. Also, in some stents, during plastic deformation of the stent (i.e. balloon expansion) the strain is concentrated at small zones. This limits the properties of the material that can be used as well as the radial force and the expansion rate.

U.S. Pat. No. 5,776,161 issued to Globerman, which is incorporated by reference herein in its entirety, addresses a number of these issues. Globerman discloses an expandable stent having a small initial diameter, flexibility along its longitudinal axis prior to expansion and minimization of rigid local strain on the stent material by the presence of rotation joints which have minimal strain during stent expansion. The stent is substantially the same length before and after expansion and being flexible longitudinally when constrained, it is easy to deliver. However additional improvements in longitudinal flexibility in the crimped stent during delivery and scaffolding after delivery are still desired.

SUMMARY OF THE INVENTION

These and other objects are accomplished by the present invention. The medical device of the present invention includes a catheter and a stent mounted on the catheter, the stent having a hollow, cylindrical body made with a plurality of rings. The rings each extend circumferentially around the cylindrical body and include an undulating series of peaks and valleys. Typically, the undulating peaks and valleys of the rings are formed by opposing curved segments joined to each other by substantially straight segments. The rings are joined together by a series of links which are shaped and arranged to promote longitudinal flexibility as the stent is delivered on the catheter and effective scaffolding after deployment and to prevent shortening of the stent as the stent is expanded.

In one aspect of the invention, the rings are provided with inflection points on some portions of the rings which extend between an adjacent peak and valley of the ring. At each inflection point, a portion of the ring extends in a generally circumferential direction for a short distance. Typically, the inflection point is substantially centered between a peak and a valley of the ring. A link is joined at one end at the inflection point on one ring and also joined at a second end at a second inflection point on an adjacent ring. This link joins the rings together. Preferably, the link includes at least two curved segments in the unexpanded device which are capable of deflecting to promote the tendency of the stent to flex longitudinally when it is subjected to bending forces such as those encountered during delivery of the stent and catheter through a tortuous coronary artery. Also preferably, the short portion of the ring at the inflection point which extends generally circumferentially has a length measured circumferentially which is at least as great as the width of the link to which it is attached. Preferably, the circumferential length is no more than about twice the width of the link to which it is attached. This promotes the scaffolding provided to the vessel by the expanded stent since the links can be fit together closely in a nested arrangement with the undulations of the rings as the stent is crimped on the balloon catheter. By "nest", "nested" or nesting" herein we mean that the elements are conformally arranged such they can be in very close proximity when the stent is crimped onto the catheter but without substantial contact that would affect the ability of the various elements to move in relation to each other as the stent and catheter are advanced through a tortuous body vessel. Where the undulations of the ring include generally straight segments between the peaks and valleys, the straight segments may be interrupted by an inflection point which produces a offset portion in the straight segment in a generally circumferential direction. In some preferred embodiments of the invention, no more than one link is connected to either of the first and second inflection points. This makes the inflection point a "dead end" in the longitudinal extent of the connecting links for the stent and permits some of the flexing forces which are not absorbed by the link itself to be absorbed by the rings to which it is attached. The links can be arranged to provide flexibility whether the peaks and valleys of the rings are arranged to make the rings appear to be mirror images to each other (i.e. peaks line up with or closely approach each other) or whether the peaks and valleys are paired with each other in an in-phase relationship or any alignment of the rings intermediate to those positions. Preferably, the rings are joined by multiple links (most preferably 3 or more) and have the same number of inflection points on each ring as the number of attaching links. When a large number of connecting links are employed, any curves or bends in the links are preferably of a complimentary shape to each other such that they will nest together when the stent is crimped onto the catheter.

Another aspect of the invention is the conformal nesting of ring and link components such that the stent can be readily crimped onto a balloon or other expansion device on the catheter. The stent made according to the present invention may be made from a tube which is cut with lasers or other techniques which are well known to those skilled in the art. The initial pattern cut into the tube includes link and ring components which cooperate with each other but which provide sufficient spacing between components that the stent can be crimped onto a catheter without causing general abutment of the ring and link components with each other and also permit longitudinal movement of the link components without disturbing the crimp of the ring components on the catheter during deployment of the stent through tortuous coronary arteries. The need for spacing between the components in the crimped condition must be balanced with the need to provide improved scaffolding of the vessel being treated. A relatively abundant number of links provides improved scaffolding of the vessel but potentially interferes with the ability to crimp the stent onto the catheter. In the present invention, the inflection points can provide the spacing needed for the nesting of the ring and link components by extending the ring in a generally circumferential direction for a distance which is sufficient to accommodate the width of the link component and provide space needed between the link components and the ring components which allows the stent to be crimped onto the catheter. In some embodiments of the invention, each inflection point includes an attachment to two connecting links extending in opposing directions and the circumferential offset at the inflection point provides for nesting of both connecting links with the ring components on the opposite sides. Thus, in the present invention, large numbers of connecting links can be included within a crimpable stent design.

Another aspect of the invention is to provide flexibility in the stent crimped on the catheter such that the stent can flex near the inflection points without significant radial expansion as the stent is subjected to bending along a longitudinal axis as it is advanced through bends in a coronary artery. As stents are advanced through tortuosities of a vessel, they are subjected to bending forces which can produce longitudinal stresses on the connector links. If the movement of connector links pulls the undulations open from their crimped position, the stent can become radially enlarged and have difficulty in crossing a narrow lesion. The present invention reduces the potential for this problem by aligning the connection of the links with the rings at a short, circumferentially extending portion, by providing curvature in the links which are then able to flex and thereby reduce stress on the junctions between the rings and the links and by providing "dead end" connections with the links which then avoids the transmission of forces from ring to ring throughout the length of the stent.

Yet another aspect of the invention is in connection with the stent configuration in which the undulating peaks and valleys of the rings are oriented such that the rings have peaks and valleys which are paired with each other in an in-phase relationship. In such a configuration, a link can be provided which interconnects with the rings at points on the rings which are substantially centered between the respective peaks and valleys of the rings and yet allows the link to nest within the peaks and valleys of the rings. This can be accomplished by providing at least two curved segments in the link in a central portion of the link.

Yet another aspect of the invention is in connection with the stent configuration in which the undulating peaks and valleys of the first ring are arranged with the undulating peaks and valleys of the second ring such that the first and second rings appear as mirror images of each other. In such a configuration, a link can be provided which interconnects with the rings at points on the rings which are substantially centered between the respective peaks and valleys of the rings and yet allows the link to nest within the peaks and valleys of the rings. This can be accomplished by providing a link including a sharp radius segment at each end and a gently curved central segment.

BRIEF DESCRIPTION OF THE DRAWINGS

FIG. 1 is an elevational view of a balloon catheter with a stent mounted on the balloon portion of the catheter.

FIGS. 2–5 are flattened plan views showing portions of stents made according to the present invention. Each of the stent patterns shown would be curved into a cylindrical shape as applied to the balloon catheter as shown in FIG. 1.

FIGS. 5–14 are flattened plan views showing stents made according to the present invention. Each of the stent patterns shown would be curved into a cylindrical shape as applied to the balloon catheter as shown in FIG. 1.

DESCRIPTION OF THE PREFERRED EMBODIMENTS

Figure 5:
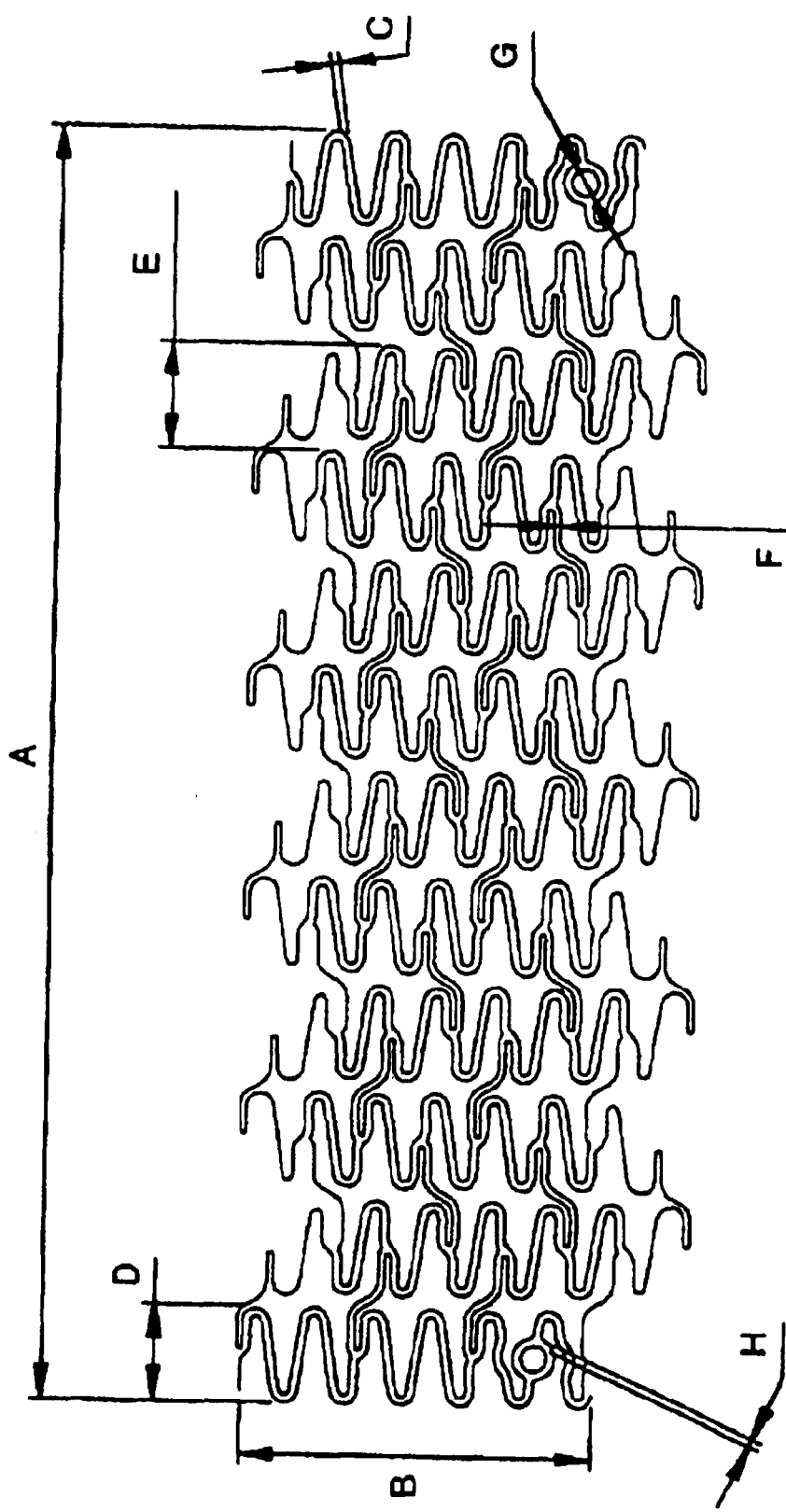

Referring now to FIG. 1, the medical device 1 of the present invention includes a catheter 2 and a stent 3 mounted on the catheter 2 in an unexpanded condition. The stent 3 has a hollow, cylindrical body made with a plurality of rings. As shown, the stent 3 is crimped over a balloon 4 affixed to the catheter 2 near the distal end of the catheter 2. The stent 3 can include a variety of configurations as shown in FIGS. 2 to 14 which are shown in an open and flattened configuration as they would appear in an unexpanded and uncrimped condition. The balloon 4 can be practically any balloon suitable for angioplasty procedures and capable of inflation to 8 atmospheres of pressure. A preferred type of balloon 4 is a balloon with multiple folds which permits the stent to expand evenly that is approximately the same length as the stent. In addition to crimping, the stent 3 can be held onto the balloon 4 by retention techniques that are well known to those skilled in the art.

Referring now also to FIG. 2, rings 10a–c are shown. Each of the rings 10a–c extend circumferentially around the cylindrical body of the stent 3 and include an undulating series of peaks 11 and valleys 12. The undulating peaks 11 and valleys 12 of the rings 10a–c are formed by opposing curved segments 13a–b joined to each other by substantially straight segments 14. The rings 10a–c are joined together in a repeating pattern by a series of links 15 which are shaped and arranged to promote longitudinal flexibility as the stent is delivered on the catheter and effective scaffolding after deployment. In connection with the stent 3 configuration of FIG. 2, it should be noted that the configuration of undulating peaks 11 and valleys 12 of the rings 10a–c are oriented such that the rings have peaks 11 and valleys 12 which are paired with each other in an in-phase relationship. In this configuration, a link 15 can be provided which interconnects with the rings 10a–c at points 16a–b on the rings 10a–b which are substantially centered between the respective peaks 11 and valleys 12 of the rings 10a–c and yet allows the link to nest within the peaks 11 and valleys 12 of the rings 10a–c as the stent is crimped onto the balloon 4 of the catheter 3. This is accomplished in part by providing at least two curved segments 17a–b in the link in a central portion of the link 15. As shown in FIG. 2, no more than one link 15 is connected to either of the points 16a–b. This makes the points 16a–b "dead ends" in the longitudinal extent of the connecting links 15 for the stent 3 and permits some of the flexing forces which are not absorbed by the link 15 itself at the curved segments 17a–b to be absorbed by the rings 10a–c to which it is attached. The nesting of link 15 and ring 10a–c components is also made possible by providing only three of the links 15 attaching each of the rings 10a–c to its immediate neighbor. This leaves some of the straight segments 14 without connections and the links are spaced-apart such that no links 15 have adjacent connections to the rings 10a–c which oppose each other. A radiopaque marker 18 is joined to ring 10a inside a circular land portion 19a link 15a joins the land portion with the adjacent ring 10b such that the link 15a resides between two peaks of ring 10a such that it will not interfere with the ring as the stent 3 is crimped onto the balloon 4 of the catheter 2.

Referring now to FIGS. 1 and 3, in another embodiment of the invention, the rings 20a–c are provided with inflection points 21 on some portions of the rings 20a–c which extend between an adjacent peak 22 and valley 23 of the rings 20a–c. At each inflection point 21, a portion of the ring extends in a generally circumferential direction (indicated generally 24) for a short distance. The inflection point 21 is shown substantially centered between a peak 22 and a valley 23 of the rings 20a–c. A link 25 is joined at one end at the inflection point 21 a on one ring 20a and also joined at a second end at a second inflection point 21b on an adjacent ring 20b. This link 25 joins the rings 20a–b together. Each link 25 includes at least two curved segments 26a–b in the unexpanded stent 3 which promote the tendency of the stent 3 to flex longitudinally when it is subjected to bending forces such as those encountered during delivery of the stent 3 and catheter 2 through a tortuous coronary artery. It can be seen in FIG. 3 that the short portion of the rings 20a–c at the inflection point 21 which extends generally circumferentially has a length measured circumferentially which is about equal to a width of the link 25 to which it is attached. This promotes the scaffolding provided to the vessel by the expanded stent 3 since the links 25 can be fit together closely in a nested arrangement with the undulations of the rings 20a–c as the stent 3 is crimped on the balloon 4 of the catheter 2. When as shown in FIG. 3, the undulations of the rings 20a–c include generally straight segments 27 between the peaks 22 and valleys 23, the straight segments 27 are interrupted by an inflection point 21 which produces a offset portion in the straight segment 27 in a generally circumferential direction 24. Only one link 25 is shown to be connected to either of the inflection points 21a–b. This makes the inflection point 21 a "dead end" in the longitudinal extent of the connecting links 25 for the stent 3 and permits some of the flexing forces which are not absorbed by the link 25 itself to be absorbed by the rings 10a–c to which it is attached. The links 25 can be arranged to provide flexibility whether the peaks 22 and valleys 23 of the rings 20a–c are arranged to make the rings 20a–c appear to be mirror images to each other (i.e. peaks line up with or closely approach each other) or as shown here where the peaks 22 and valleys 23 are paired with each other in an in-phase relationship or any alignment of the rings intermediate to those positions. The rings 20a–c are joined by multiple links 25 (preferably 3 or more to provide good scaffolding) and are shown to have the same number of inflection points 21 on each ring 20a–c as the number of attaching links 25. When a large number of connecting links 25 are employed, any curves or bends in the links 25 are preferably of a complimentary shape to each other such that they will nest together when the stent 3 is crimped onto the balloon 4 of the catheter 2. It should also be noted in FIG. 3 that the end ring 20a includes a radiopaque marker 28 which provides fluoroscopic confirmation of the position of the stent 3 when it is advanced into the patient. The adjacent ring portions are provided with curved segments 29*a–b* which permit them to nest with the circular form of the marker 28 as the stent 3 is crimped onto the balloon 4 of the catheter 2.

Referring now to FIGS. 1 and 4, in yet another embodiment of the invention, the rings 30*a–c* of the stent 3 have undulating peaks 31 and valleys 32 arranged with the undulating peaks 31 and valleys 32 of an adjacent rings 30*a–c* such that the rings 30*a–c* appear as mirror images of each other. In such a configuration, a link 33 can be provided which interconnects with the rings 30*a–c* at points on the rings which are substantially centered between the respective peaks 31 and valleys 32 of the rings 30*a–c* and yet allows the link 33 to nest within the peaks 31 and valleys 32 of the rings. This can be accomplished by providing a link 33 which includes a sharply curved segment 34*a–b* at each end and a straight or gently curved central segment provided that it is connected at a "dead end" where only one link 33 is connected at any one ring segment between a peak 31 and valley 32. As shown, such a link 33 can also nest with the opposing ring segments as the stent 3 is crimped onto the balloon 4 of a catheter 2. Also shown in FIG. 4 is the adjustment in the relative amplitudes of the undulations between the rings 30*a–c*. Ring 30*a* is shown to have a smaller amplitude in dimension "A" than the amplitude of ring 30*b* as shown in dimension "B". This variation in amplitude can be particularly important in stent designs where the stent 3 may tend to flare at the ends as the stent is advanced through tortuous arteries since the lower amplitude ring 30*a* at the end of the stent 3 will have a reduced tendency to be deformed and tip outward when the stent 3 is subjected to longitudinal bending forces. The lower amplitude ring 30*a* can be on a distal or proximal end of the stent 3. The person skilled in the art will appreciate that this can be especially important in situations where one advances the stent 3 and catheter 2 through a tortuous artery but, instead of deploying the stent 3, then wishes to withdraw the stent 3 into the guide catheter while it is still crimped on the balloon 4. If the end of the stent 3 has become flared during the failed deployment, it can catch on the distal edge of the guide catheter as it is being withdrawn.

Referring now to FIGS. 1 and 5, a full pattern of a stent 3 for a coronary artery application is shown which is substantially the same pattern which was discussed above in connection with FIG. 3. The stent 3 has a length "A" which can be about 8 to 30 mm (and as depicted could be about 15–25) mm for a coronary artery application although those skilled in the art will appreciate that the pattern can be configured to give many lengths. The dimension "B" refers to the circumference of the stent 3 for a coronary application which can be about 3–7 mm and gives an uncrimped diameter for the stent 3 of about 1–2 mm. The dimension "C" refers to the width of one of the rings which in this example could be in the range of about 0.08 to 0.12 mm. The dimension "D" refers to the amplitude of one of the rings and in this example could be in the range of about 0.75 to 2.5 mm. The dimension "E" refers to the peak-to-peak spacing for the rings and in this example could be in the range of about 1–3 mm. The dimension "F" refers to the width of a connecting link and in this example could be in the range of about 0.06 to 0.1 mm. The dimensions G and H refer to the diameter of the radiopaque marker and the width of the portion of the ring holding the marker. This stent 3 can be made by laser cutting from a tube of stainless steel or other suitable material by methods which are well known by those skilled in the art. Similar structures are marked with the same dimensional symbols ("A" to "H") in each of the drawings FIGS. 5–14 for the convenience of the reader.

Figure 6:
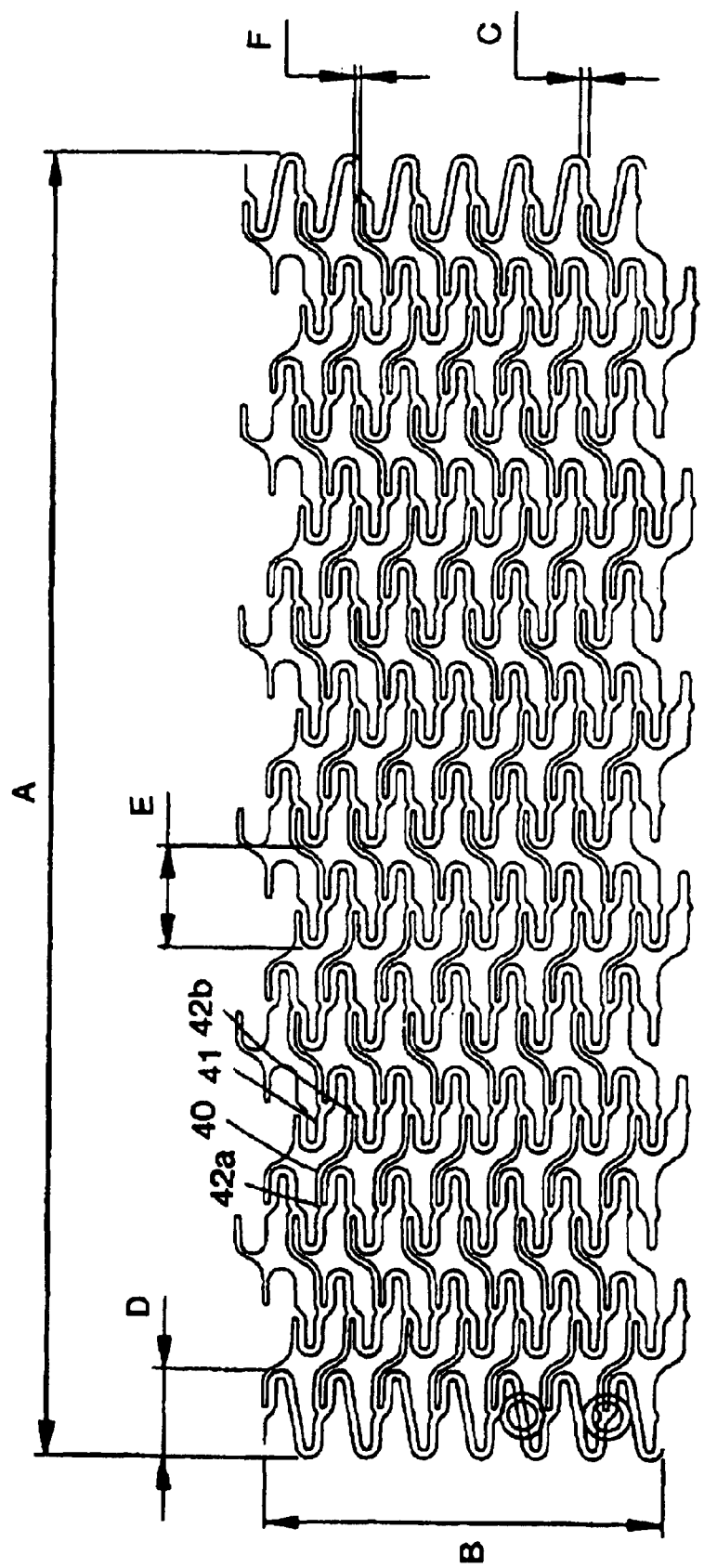

Referring now to FIG. 6, the stent 3 of FIG. 5 has been modified by the addition of more connecting links 40 and the use of shorter amplitude rings 41 (i.e. reductions in dimensions "D" and "E") in combination with reductions in the widths in various components (i.e. reductions in dimensions "C" and "F") in order to provide better crimp profile, flexibility and scaffolding. It should be noted in connection with FIG. 6 and other drawing figures that the links 40 can vary somewhat in width along their length in order to modify or direct the way in which the link 40 can flex as the stent 3 is deployed through a tortuous body lumen. In this embodiment of the stent 3, the ends of the links 40 flare out just before the connection points 42*a–b* in order to provide increased resistance to flexing near the connection points 42*a–b*.

Figure 7:
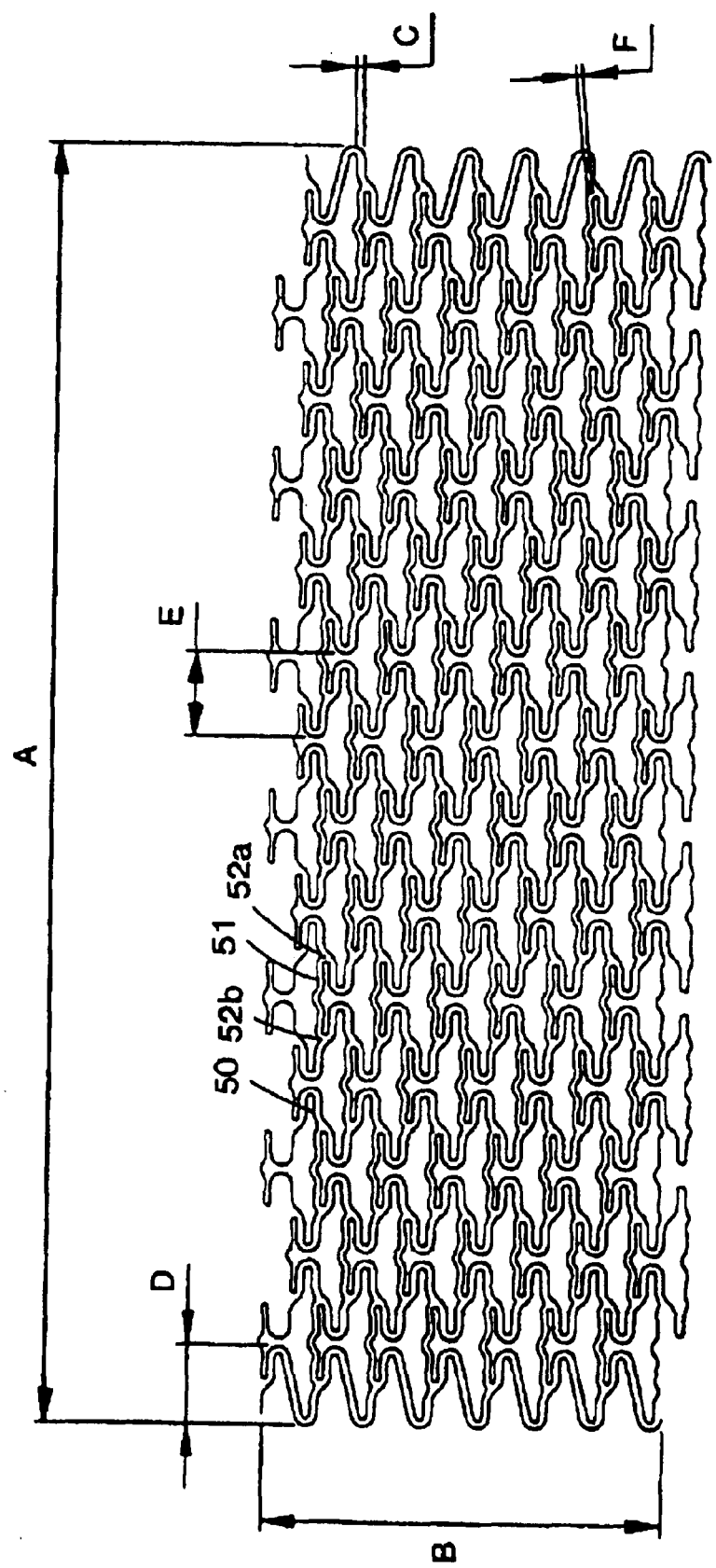

Referring now to FIG. 7, the stent 3 is made in a configuration which combines features shown in the stents 3 of FIGS. 3 and 4. The stent 3 employs rings 50 which are arranged in a mirror image configuration. Connecting links 51 are connected to rings 50 at inflection points 52*a–b* with a slightly curved connecting link 51 which provides improved flexibility. The connecting links 51 "dead end" at the inflection points 52*a–b* to also provide flexibility. The number of rings 50 are increased and the amplitude of the rings 50 is reduced (i.e. reductions in dimensions "D", "E", "C" and "F"). Thus the "cell" size ( i.e. the size of the smallest repeating unit in the pattern) is reduced and scaffolding is improved.

Figure 8:
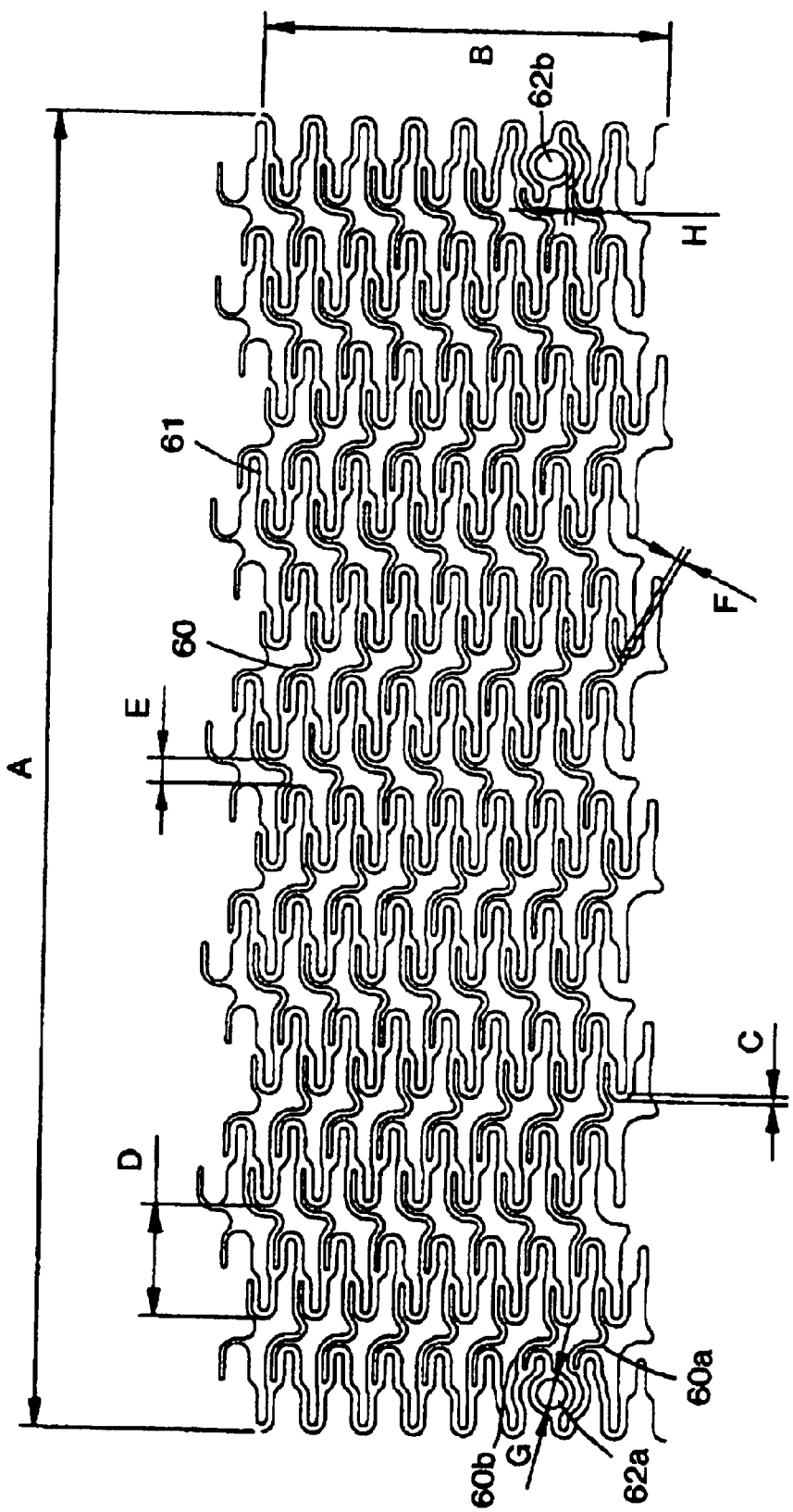

Referring now to FIG. 8, the stent 3 of FIG. 6 is modified by adding a longer and more highly curved link 60 and by adding another two bends in the undulation in each of the rings 61. The resulting stent 3 had improved scaffolding from smaller cell size and more flexibility from the more curved link 60. Radiopaque markers 62*a–b* nest with the adjacent ring elements as the stent 3 is crimped onto the balloon 4 of the catheter 2. In addition, the links 60*a–b* connecting the ring immediately adjacent to the radiopaque markers are shorter than the other links and are attached to the ring at a portion of the ring away from the radiopaque marker 62*a*. This provides the markers 62*a–b* with additional space and ring flexibility to permit improved crimping of the stent 3 onto the balloon 4.

Figure 9:
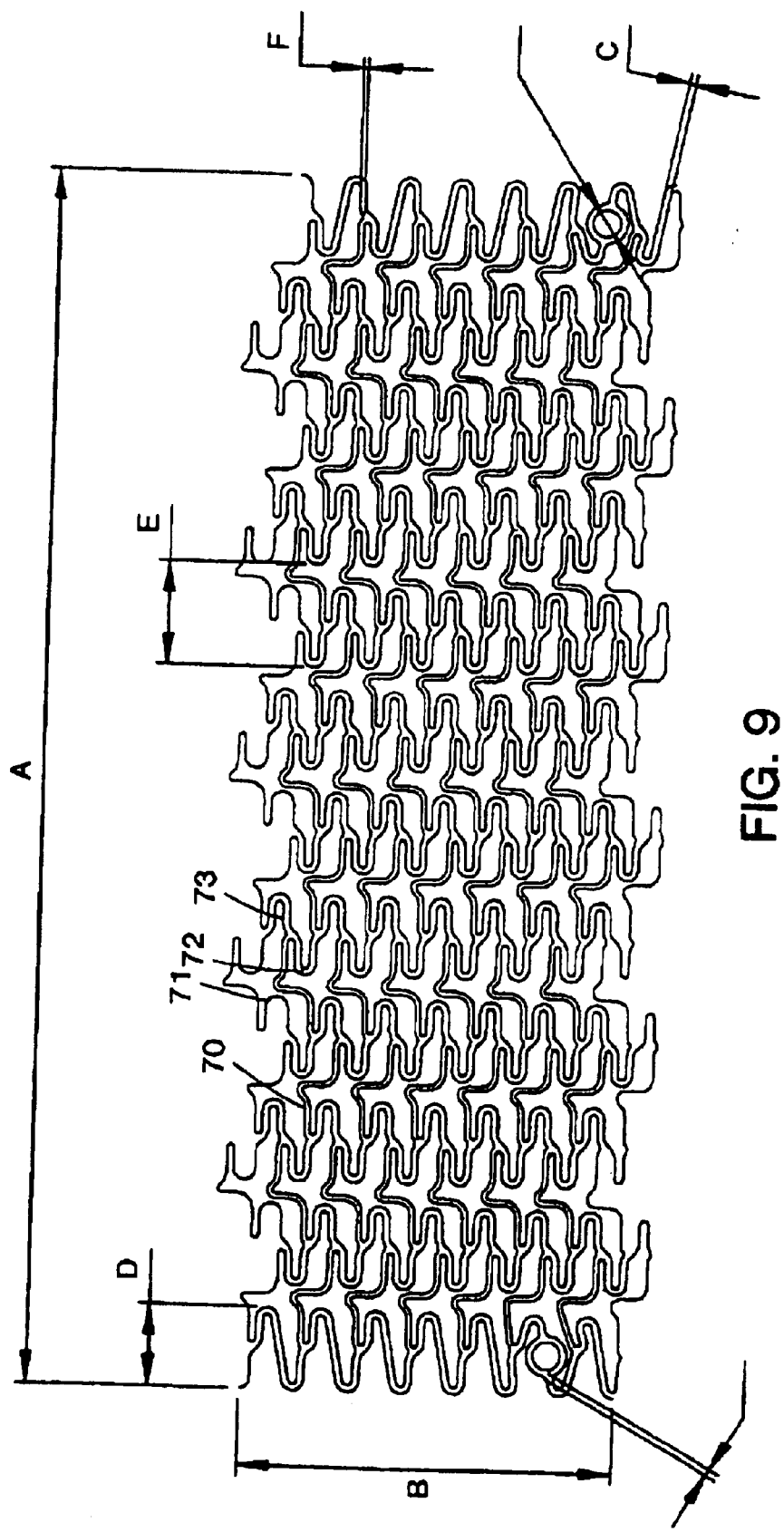

Referring now to FIG. 9, the stent 3 is a maximum flexibility version of the stent 3 of FIG. 8 made by making the connecting link 70 even more curved and increasing the cell size to permit the link 70 to flex in the space between the peaks 71 and valleys 72 of adjacent rings 73.

Figure 10:
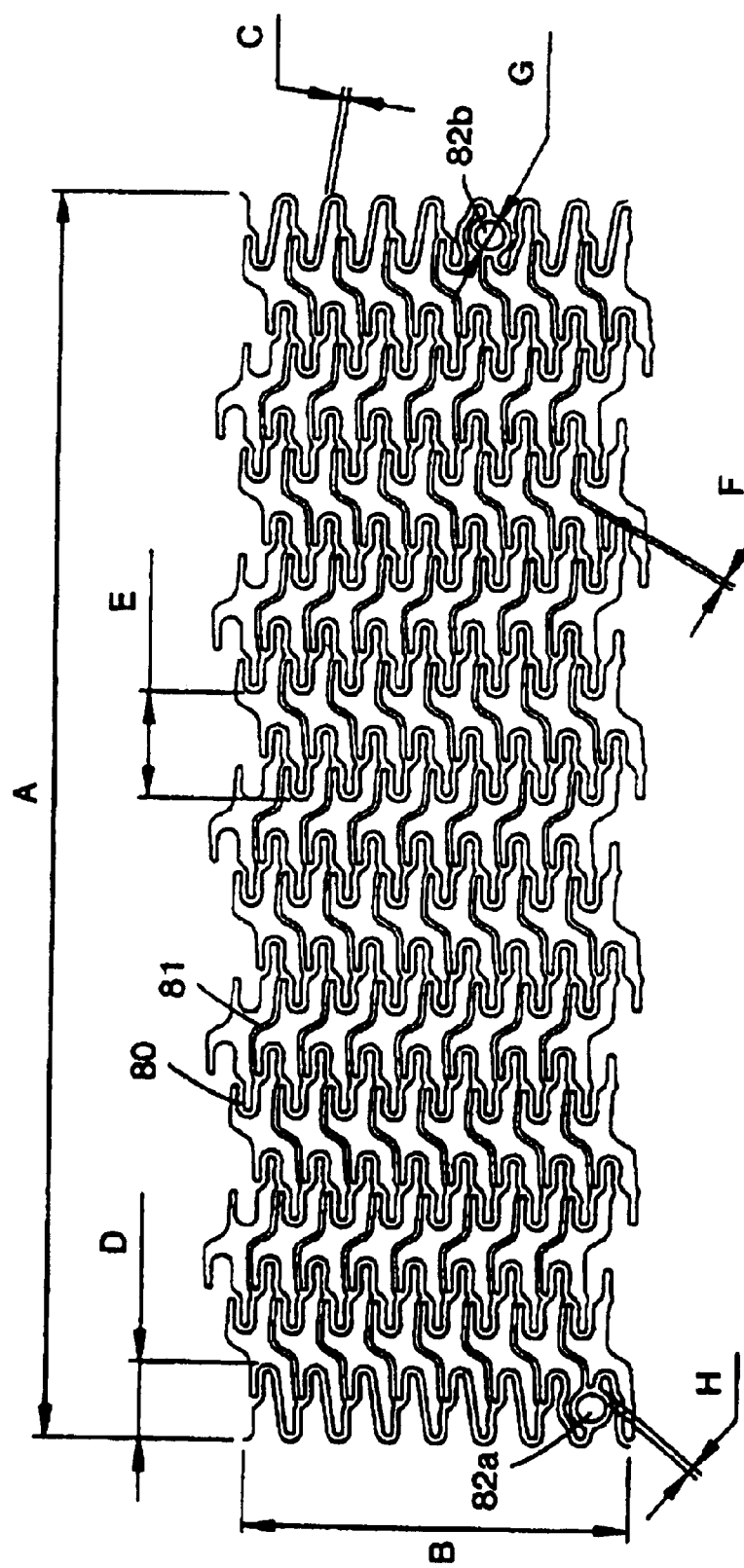

Referring now to FIG. 10, the stent 3 is a variant of the stent 3 of FIG. 6 in which the dimension "D" is relatively smaller in relation to dimension "E" such that more space is available between the rings 80 so that the stent 3 can flex with maximum clearance between those components when the stent 3 is deployed in the bend of a body lumen. Radiopaque markers 82*a–b* are located at opposite ends of the stent 3 to allow the physician to precisely identify the position of the ends of the stent 3 fluoroscopically while the stent 3 is being deployed into the patient. The markers 82*a–b* can take the form of a thin gold disk set into an portion of the pattern. The markers 82*a–b* have their highest fluoroscopic visibility when looking directly down onto the flat plane of the disk and lesser visibility when looking at the edge of the disk. Therefore, the markers 82*a–b* can be aligned with each other so as to both be visible at the same intensity no matter what the rotational orientation of the stent (as shown in FIG. 9) or offset (shown in FIG. 10 about 90 degrees offset) with regard to each other to permit at least one marker 82a–b to always be viewed in its highly observable flat orientation. More markers can be added to those shown in FIGS. 9–10 so that each end of the stent 3 has two or more markers in a relative offset position which then permits one of the markers at each end to always be brightly observable no matter what rotational orientation the stent 3 is in.

Figure 11:
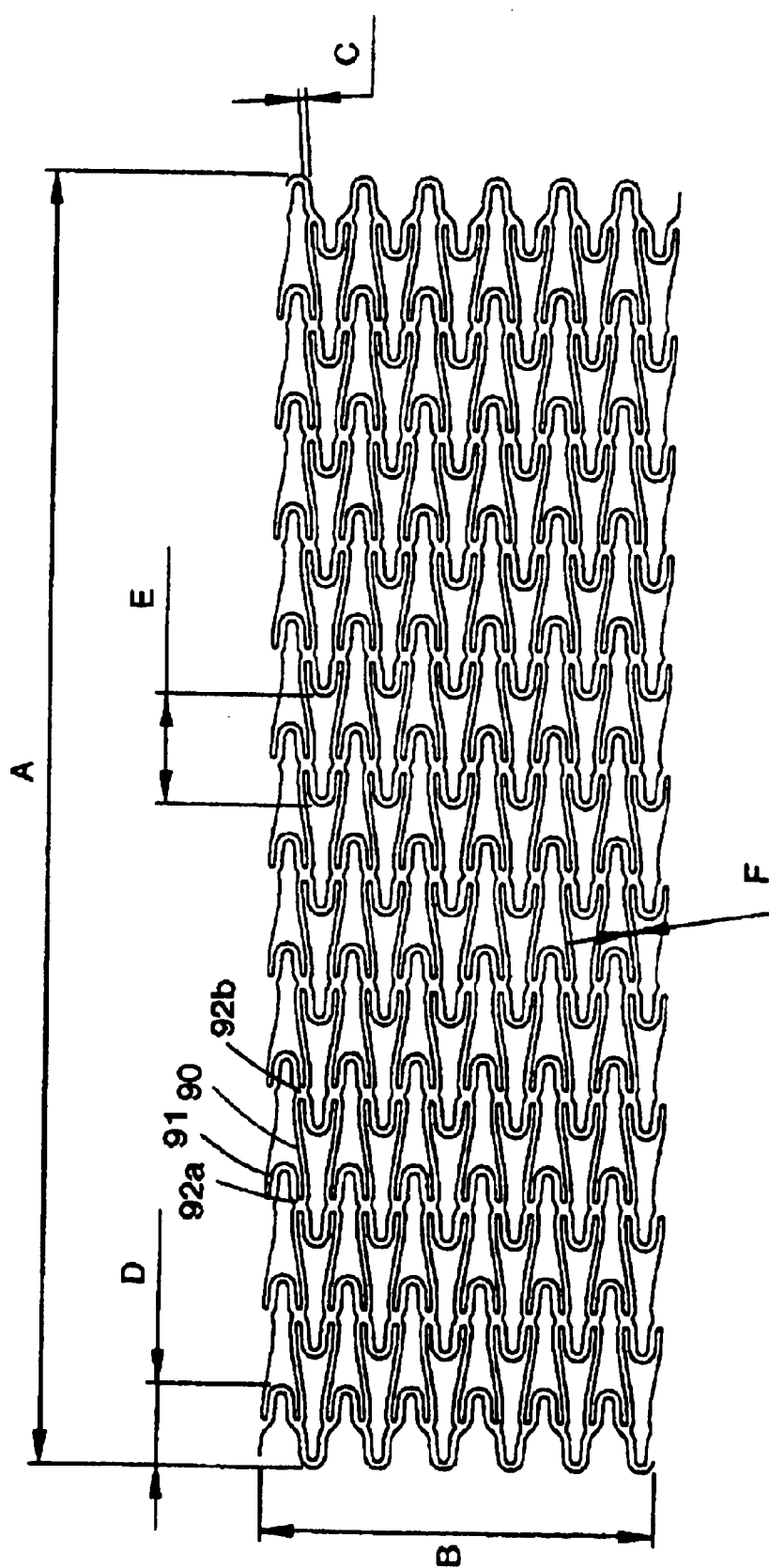

Referring now to FIG. 11, the stent 3 is a variant of the stent 3 of FIGS. 3 and 4 with long, relatively straight links 90 joined with rings 91 at inflection points 92a–b. It should be noted that in the center of the pattern two links 90 are joined at each inflection point 92a–b on opposing sides without compromising the ability of the ring 91 and link 90 elements to nest as the stent 3 is crimped onto the balloon 4 of the catheter 2. The use of multiple links 90 at each inflection point 92a–b provides a greater number of links 90 overall and a therefore a greater amount of scaffolding in the expanded stent 3 than in other designs.

Figure 12:
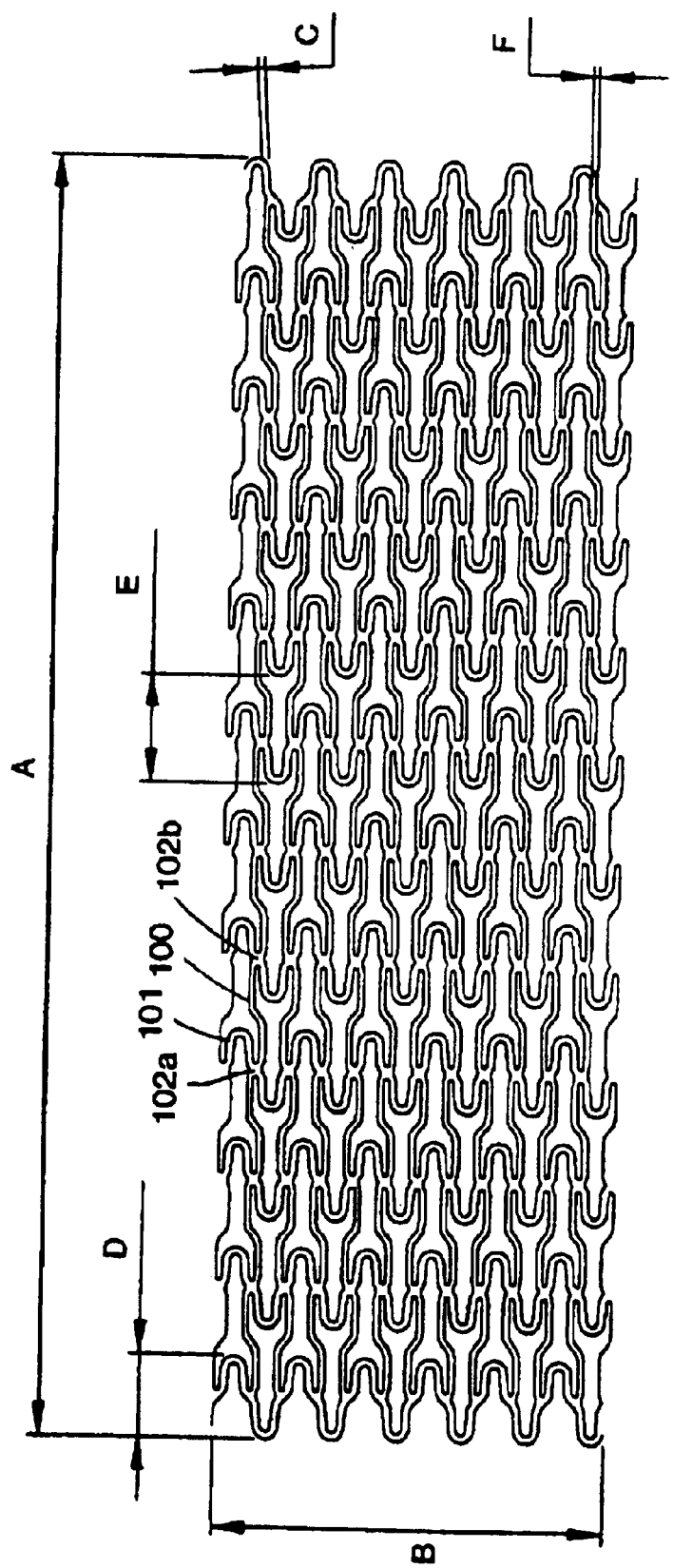

Referring now to FIG. 12, the stent 3 is a variant of the stent 3 of FIGS. 3 and 12 with curved connecting links 100 replacing the straighter links in FIG. 12. Again, the links 100 are connected to the rings 101 at inflection points 102a–b such that more than one link 100 is attached at each inflection point 102a–b.

Figure 13:
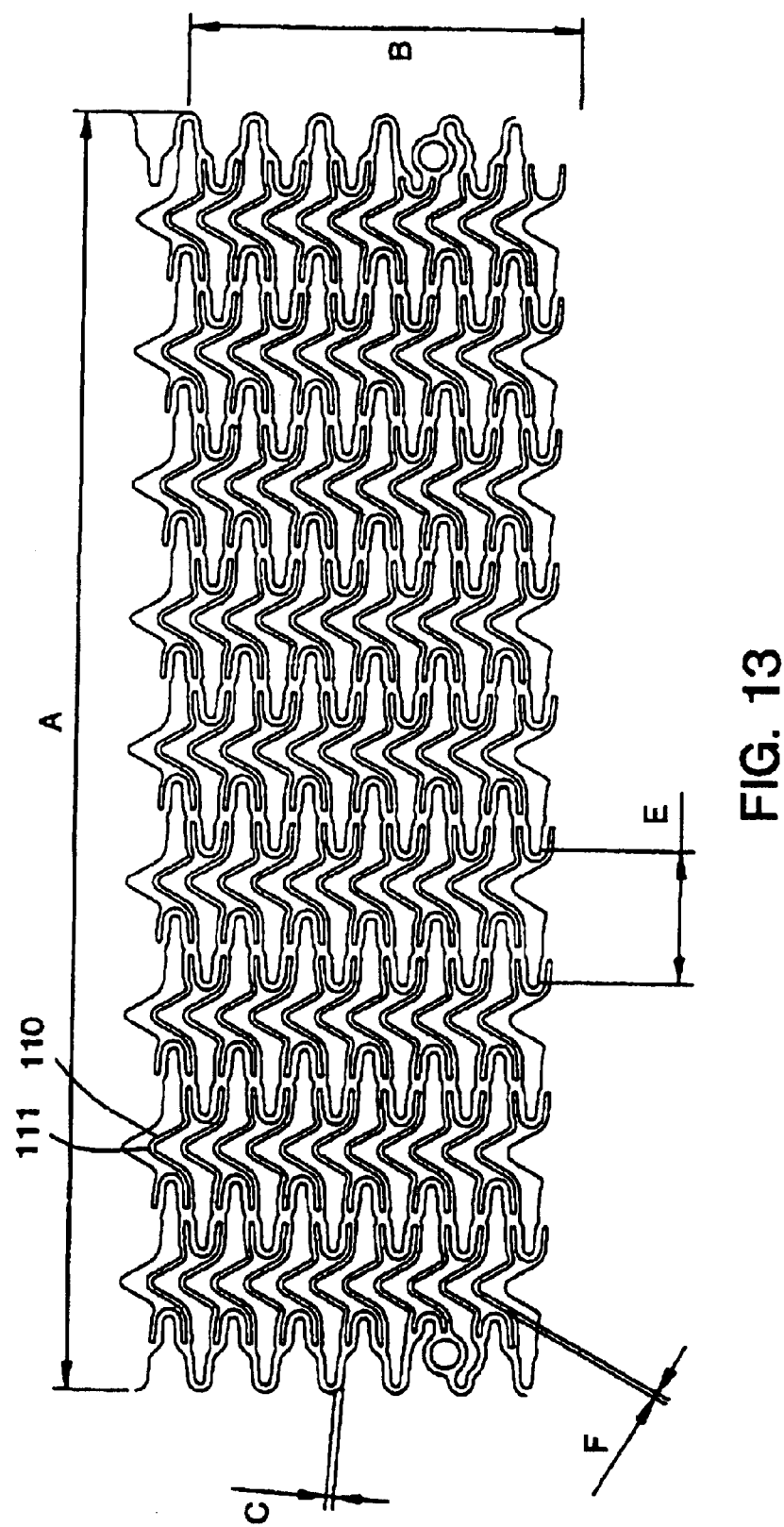

Referring now to FIG. 13, the stent 3 is a variant of the stent 3 of FIG. 12 in which a longer and more curved link 110 is used to improve flexibility of the stent 3. The links 110 include a peaked portion 111 which extends in the circumferential direction of the stent 3. It is important to note that the links 110 have peaked portions which have the ability to conform to each other and nest as the stent 3 is crimped onto the balloon 4 of the catheter 2.

Figure 14:
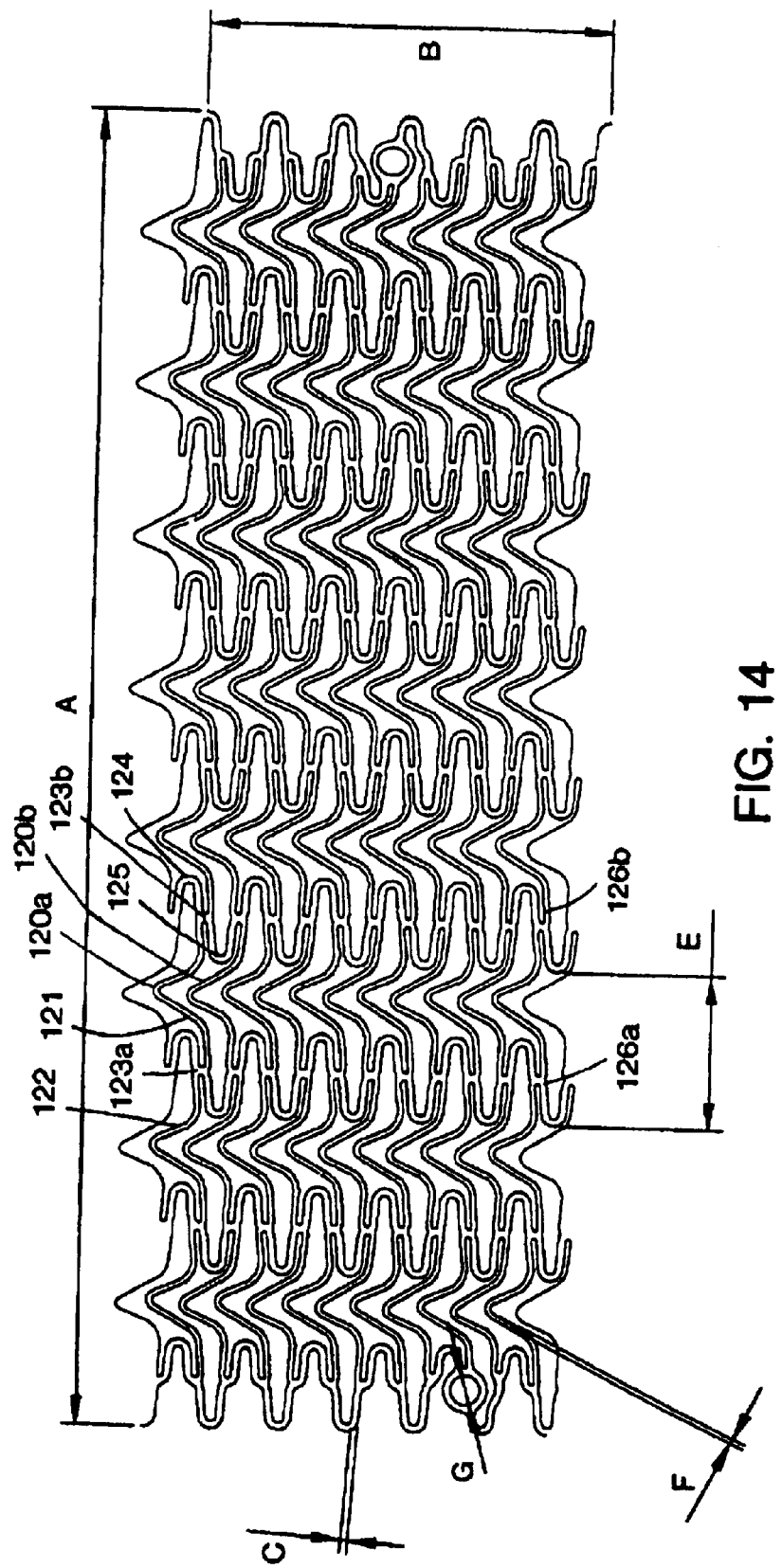

Referring now to FIG. 14, the stent 3 is a variant of the stent 3 of FIG. 13 in which the cell size is increased slightly and the shape of the peaked portion 120a–b of each link 121 are altered so that the adjacent peak portions 120a–b will conform and nest better when the stent 3 is crimped. It will be noted that every peak portion 120a–b is slightly offset from its nearest neighbor to compensate for the slight alteration in the shape of the link 121 that takes place as the stent 3 is crimped. This provides a more precise nesting of the links 121 in the crimped stent 3. Also to be noted in connection with FIG. 14 is the relative position of the connecting links 121, 122 with respect to the inflection point 123a. The first connecting link 121 is connected to the inflection point 123a at a lower portion of the inflection point 123a while the second connecting link 122 is connected at an opposite side of the inflection point 123a at an upper portion of the inflection point 123a. With the in-phase arrangement of peaks 124 and valleys 125 in this pattern, the connecting links 121, 122 are connected to adjacent rings 126a–b such that a link 121 connects at one end to one ring 126a at a lower portion of the inflection point 123a and at the other end at an upper portion of the inflection point 123b. Also to be noted in the pattern of FIG. 14 is that each peak 124 and each valley 125 has two connecting links 121, 122 extending laterally past them to join with another ring 126a–b. The connecting links 121, 122 proceed from one end attachment at an inflection point 123a–b such that they parallel the portion of the ring 126a–b and are positioned such that when the stent 3 is expanded they will extend outward from the inflection point 123a–b and assist in the scaffolding provided by the central portion of the ring 126a–b. The connecting links 121, 122 also extend past the peak 124 or valley 125 components to extend the scaffolding provided by the peak 124 and valley 125 components of the rings 126a–b toward the next ring. In particular, the connecting links 121, 122 extend upwardly past the peak 124 and valley 125 portions of the rings 126a–b into peaked portions 120a–b. This arrangement provides highly effective scaffolding for the stent 3 when it is expanded against a body lumen of the patient.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. Accordingly, the present invention is not limited to the particular embodiments which have been described in detail herein.

We claim:

1. A medical device comprising:
   a catheter and a stent mounted on the catheter, the stent comprising a hollow, cylindrical body comprised of a first ring and a second ring, the first and the second rings each extending circumferentially around the cylindrical body, the first and second rings each including an undulating series of peaks and valleys;
   a first inflection point on the first ring, the first inflection point disposed on an intermediate portion of the first ring substantially centered between an adjacent peak and valley, the first inflection point including a portion extending generally circumferentially;
   a second inflection point on the second ring, the second inflection point disposed on an intermediate portion of the second ring substantially centered between an adjacent peak and valley, the second inflection point including a portion extending generally circumferentially;
   a link joined at a first end at the first inflection point on the first ring and at a second end at the second inflection point whereby the first and second rings are joined together.

2. A medical device as in claim 1 wherein the link includes at least two curved segments.

3. A medical device as in claim 1 wherein the portion of the inflection point extending generally circumferentially has a length measured circumferentially which is substantially equal to a width of the link to which it is attached.

4. A medical device as in claim 1 wherein the stent is crimped onto a distal portion of the catheter.

5. A medical device as in claim 4 wherein a portion of the link near its first end nests within the undulating series of peak and valleys of the first ring of the crimped stent.

6. A medical device as in claim 4 wherein the crimped stent can flex near the first and second inflection points without significant radial expansion as the stent is subjected to bending along a longitudinal axis as it is advanced through bends in a coronary artery.

7. A medical device as in claim 1 wherein the undulating peaks and valleys of each of the first and second rings are formed by opposing curved segments joined to each other by straight segments.

8. A medical device as in claim 7 wherein at least one of the straight segments is interrupted by an inflection point which produces a generally circumferentially offset portion in the straight segment.

9. A medical device as in claim 1 wherein no more than one link is connected to either of the first and second inflection points.

10. A medical device as in claim 1 wherein the undulating peaks and valleys of the first ring are arranged with the undulating peaks and valleys of the second ring such that the first and second rings appear as mirror images of each other.

11. A medical device as in claim 1 wherein the undulating peaks and valleys the first ring are arranged with the undulating peaks and valleys of the second ring such that the first and second rings have peaks and valleys which are paired with each other in an in-phase relationship.

12. A medical device as in claim 1 wherein the first and second rings each include the same number of inflection points.

13. A medical device as in claim 1 wherein the first and second rings are joined by a plurality of links.

14. A medical device as in claim 13 wherein the plurality of links have complimentary shapes such that they will nest when the stent is crimped onto the catheter.

15. A medical device comprising:
   a catheter and a stent mounted on the catheter, the stent comprising
   a hollow, cylindrical body comprised of a first ring and a second ring, the first and the second rings each extending circumferentially around the cylindrical body, the first and second rings each including an undulating series of peaks and valleys;
   a first inflection point on the first ring, the first inflection point disposed on an intermediate portion of the first ring substantially centered between an adjacent peak and valley;
   a second inflection point on the second ring, the second inflection point disposed on an intermediate portion of the second ring substantially centered between an adjacent peak and valley;
   a link joined at a first end at the first inflection point on the first ring and at a second end at the second inflection point whereby the first and second rings are joined together;
   the stent crimped on the catheter such that the link nests near the first end within the undulating series of peaks and valleys of the first ring and also nests near the second end within the undulating series of peaks and valleys of the second ring.

16. A medical device as in claim 15 wherein the link includes at least two curved segments.

17. A medical device as in claim 15 wherein the inflection point has a length measured circumferentially which is substantially equal to a width of the link to which it is attached.

18. A medical device as in claim 15 wherein the crimped stent can flex near the first and second inflection points without significant radial expansion as the stent is subjected to bending along a longitudinal axis as it is advanced through bends in a coronary artery.

19. A medical device as in claim 15 wherein the undulating peaks and valleys of each of the first and second rings are formed by opposing curved segments joined to each other by straight segments.

20. A medical device as in claim 19 wherein at least one of the straight segments is interrupted by an inflection point which produces a generally circumferentially offset portion in the straight segment.

21. A medical device as in claim 15 wherein no more than one link is connected to either of the first and second inflection points.

22. A medical device as in claim 15 wherein the undulating peaks and valleys of the first ring are arranged with the undulating peaks and valleys of the second ring such that the first and second rings appear as mirror images of each other.

23. A medical device as in claim 15 wherein the undulating peaks and valleys of the first ring are arranged with the undulating peaks and valleys of the second ring such that the first and second rings have peaks and valleys which are paired with each other in an in-phase relationship.

24. A medical device as in claim 15 wherein the first and second rings each include the same number of inflection points.

25. A medical device as in claim 15 wherein the first and second rings are joined by a plurality of links.

26. A medical device as in claim 25 wherein the plurality of links have complimentary shapes such that they will nest when the stent is crimped onto the catheter.

27. A medical device comprising:
   a catheter and a stent mounted on the catheter, the stent composing
   a hollow, cylindrical body comprised of a first ring and a second ring, the first and the second rings each extending circumferentially around the cylindrical body, the first and second rings each including an undulating series of peaks and valleys;
   a first inflection point on the first ring, the first inflection point disposed on a portion of the first ring substantially centered between an adjacent peak and valley;
   a second inflection point on the second ring, the second inflection point disposed on a portion of the second ring substantially centered between an adjacent peak and valley;
   a link joined at a first end at the first inflection point on the first ring and at a second end at the second inflection point whereby the first and second rings are joined together;
   the stent crimped on the catheter such that the stent can flex near the first and second inflection points without significant radial expansion as the stent is subjected to bending along a longitudinal axis as it is advanced through bends in a coronary artery.

28. A medical device as in claim 27 wherein the link includes at least two curved segments.

29. A medical device as in claim 27 wherein the inflection point has a length measured circumferentially which is substantially equal to a width of the link to which it is attached.

30. A medical device as in claim 27 wherein the undulating peaks and valleys of each of the first and second rings are formed by opposing curved segments joined to each other by straight segments.

31. A medical device as in claim 30 wherein at least one of the straight segments is interrupted by an inflection point which produces a generally circumferentially offset portion in the straight segment.

32. A medical device as in claim 27 wherein no more than one link is connected to either of the first and second inflection points.

33. A medical device as in claim 27 wherein the undulating peaks and valleys of the first ring are arranged with the undulating peaks and valleys of the second ring such that the first and second rings appear as mirror images of each other.

34. A medical device as in claim 27 wherein the undulating peaks and valleys of the first ring are arranged with the undulating peaks and valleys of the second ring such that the first and second rings have peaks and valleys which are paired with each other in an in-phase relationship.

35. A medical device as in claim 27 wherein the first and second rings each include the same number of inflection points.

36. A medical device as in claim 27 wherein the first and second rings are joined by a plurality of links.

37. A medical device as in claim 36 wherein the plurality of links have complimentary shapes such that they will nest when the stent is crimped onto the catheter.

38. A medical device comprising:
a catheter and a stent mounted on the catheter, the stent comprising
a hollow, cylindrical body comprised of at least one ring, the ring extending circumferentially around the cylindrical body, the ring including an undulating series of peaks and valleys;
an inflection point on the ring, the inflection point disposed on an intermediate portion of the ring substantially centered between an adjacent peak and valley;
a first link joined at an end at the inflection point.

39. A medical device as in claim 38 wherein the inflection point includes a short portion extending generally circumferentially.

40. A medical device as in claim 39 wherein the short portion of the inflection point extending generally circumferentially has a length measured circumferentially which is substantially equal to a width of the link.

41. A medical device as in claim 38 wherein the link extends substantially parallel to a portion of the ring.

42. A medical device as in claim 38 wherein the link extends beyond a peak or valley of the ring.

43. A medical device as in claim 38 also comprising a second link joined at an end at the inflection point and extending from the inflection point in a direction substantially opposite to the first link.

44. A medical device as in claim 43 wherein the first link is joined at an upper portion of the inflection point and the second link is joined at a lower portion of the inflection point.

45. A medical device as in claim 43 wherein the first link is joined to the ring above the ring and the second link is joined to the ring below the ring.

46. A medical device as in claim 38 wherein the stent is crimped onto a distal portion of the catheter.

47. A medical device as in claim 46 wherein a portion of the link nests within the undulating series of peaks and valleys of the ring of the crimped stent.

48. A medical device as in claim 46 wherein the crimped stent can flex near the inflection point without significant radial expansion as the stent is subjected to bending along a longitudinal axis as it is advanced through bends in a coronary artery.

49. A medical device as in claim 38 wherein the undulating peaks and valleys of the ring are formed by opposing curved segments joined to each other by straight segments.

50. A medical device as in claim 49 wherein the inflection point forms an offset at at least one of the straight segments to produce a generally circumferentially offset portion in the straight segment.

51. A medical device as in claim 38 wherein the ring includes a plurality of inflection points and a plurality of links joined to the inflection points.

52. A medical device as in claim 51 wherein each peak and valley has an inflection point therebetween and a first link joined at each inflection point.

53. A medical device as in claim 52 wherein each inflection point has a second link joined at each inflection point and extending longitudinally opposite the first link.

54. A medical device as in claim 52 wherein the plurality of links have complimentary shapes such that they will nest when the stent is crimped onto the catheter.

55. A medical device as in claim 38 wherein the link varies in width.

56. A medical device as in claim 55 wherein the link is wider at the end attached to the inflection point.

* * * * *

UNITED STATES PATENT AND TRADEMARK OFFICE
CERTIFICATE OF CORRECTION

PATENT NO. : 6,730,116 B1  Page 1 of 1
APPLICATION NO. : 09/292991
DATED : May 4, 2004
INVENTOR(S) : Lone Wolinsky et al.

It is certified that error appears in the above-identified patent and that said Letters Patent is hereby corrected as shown below:

On The Title Page:
Line (75) Inventors: "Offer Nativ" should be changed to -- Ofer Nativ --

Signed and Sealed this

Second Day of January, 2007

JON W. DUDAS
*Director of the United States Patent and Trademark Office*